US009839558B2

(12) United States Patent
Blanchard et al.

(10) Patent No.: US 9,839,558 B2
(45) Date of Patent: Dec. 12, 2017

(54) ROLL-OFF FILM SYSTEM

(71) Applicant: 100% SPEEDLAB, LLC, San Diego, CA (US)

(72) Inventors: Marc Guy Blanchard, San Diego, CA (US); Ludovic Francis Boinnard, San Diego, CA (US); Kevin Michael Sigismondo, San Diego, CA (US)

(73) Assignee: 100% Speedlab, LLC, San Diego, CA (US)

( * ) Notice: Subject to any disclaimer, the term of this patent is extended or adjusted under 35 U.S.C. 154(b) by 190 days.

(21) Appl. No.: 14/701,420

(22) Filed: Apr. 30, 2015

(65) Prior Publication Data
US 2015/0328049 A1 Nov. 19, 2015

Related U.S. Application Data

(60) Provisional application No. 61/994,665, filed on May 16, 2014.

(51) Int. Cl.
*A61F 9/00* (2006.01)
*A61F 9/02* (2006.01)

(52) U.S. Cl.
CPC .............. *A61F 9/029* (2013.01); *A61F 9/025* (2013.01)

(58) Field of Classification Search
CPC ........................................ A61F 9/025
USPC .............................. D16/311; 3/311
See application file for complete search history.

(56) References Cited

U.S. PATENT DOCUMENTS

| 4,428,081 | A | * | 1/1984 | Smith | ..................... A61F 9/025 2/422 |
| 4,528,701 | A | * | 7/1985 | Smith | ....................... A61F 9/02 2/438 |
| 4,748,697 | A | | 6/1988 | Hodnett | |
| 6,073,296 | A | * | 6/2000 | Bouguerfa | ............... A42B 3/26 15/102 |
| 6,415,452 | B1 | * | 7/2002 | Watanabe | ............... A61F 9/025 2/438 |
| 6,416,177 | B1 | | 7/2002 | Gibson | |
| D691,652 | S | * | 10/2013 | Castro | .......................... D16/311 |
| 2012/0023647 | A1 | * | 2/2012 | Park | ....................... A61F 9/025 2/438 |
| 2013/0104299 | A1 | * | 5/2013 | Chen | ....................... A61F 9/029 2/431 |

(Continued)

FOREIGN PATENT DOCUMENTS

GB 2378412 2/2003
GB 2495984 5/2013

*Primary Examiner* — Khaled Annis
(74) *Attorney, Agent, or Firm* — Haynes and Boone, LLP

(57) ABSTRACT

Roll-off film systems and methods are provided in accordance with one or more embodiments that may be installed on goggle frames or adaptors to goggle frames to provide improved field of vision for users. In particular, film canisters of the roll-off film systems may include a blade section configured to seamlessly contact the goggle frame or the adaptor to the goggle frame. Further, the blade section is configured remove mud or dirt from a used section of clear film when the used section is conveyed into the film canister to prevent excess mud or dirt from entering the film canister. The blade section also is configured to slant away from the lens of the goggle to allow the mud or dirt to fall away from the field of view on the lens to provide better field of view for the user.

20 Claims, 17 Drawing Sheets

(56) References Cited

U.S. PATENT DOCUMENTS

2014/0157496 A1* 6/2014 Ginther .................. A61F 9/025
2/439

* cited by examiner

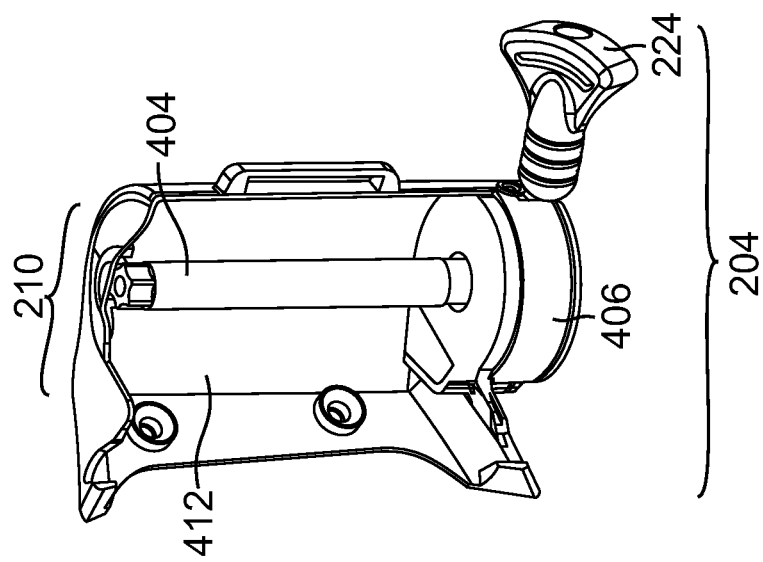
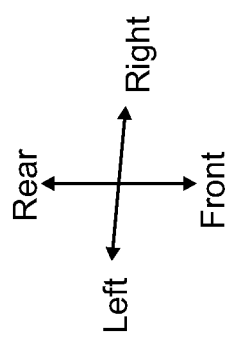
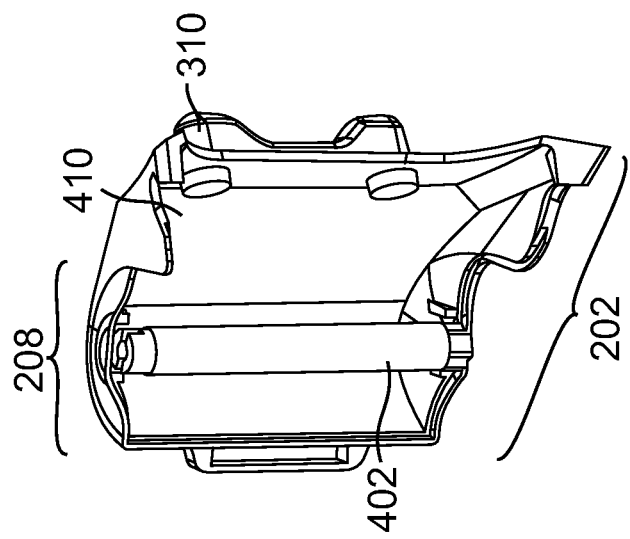
FIG. 4

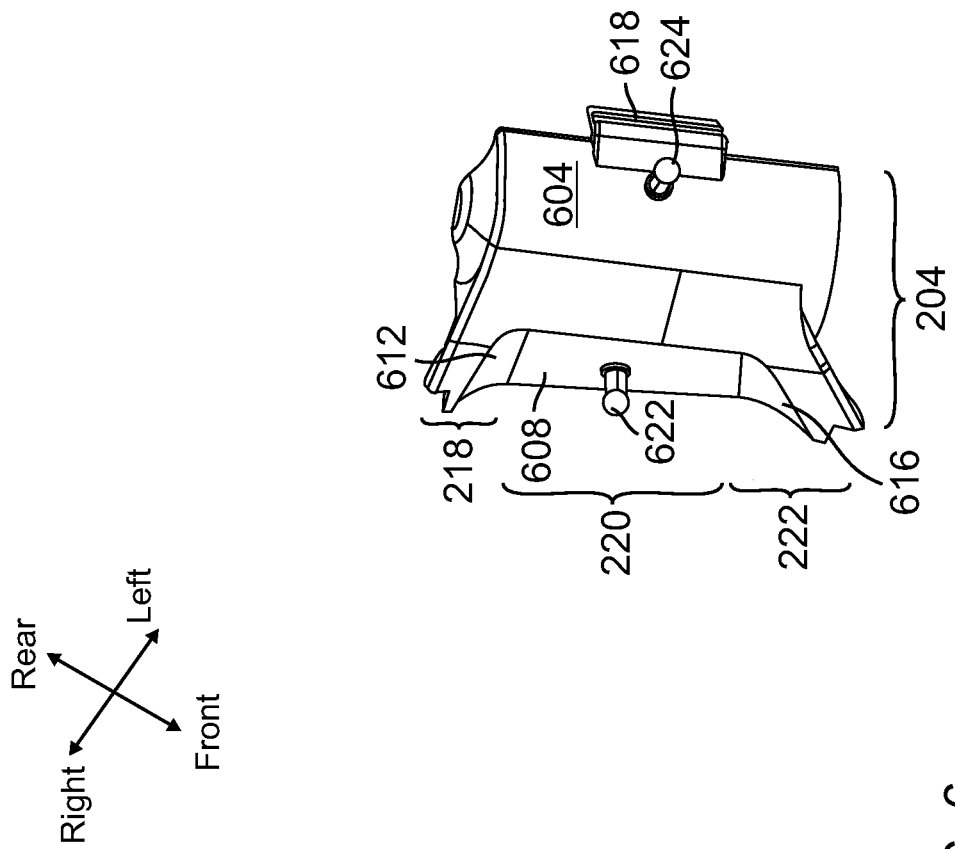
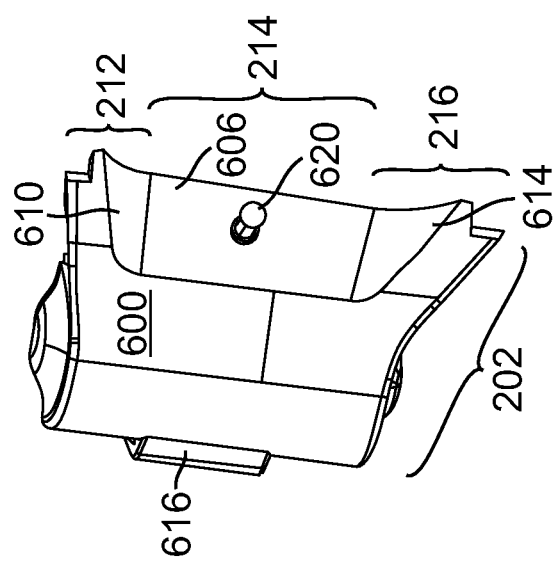
FIG. 6

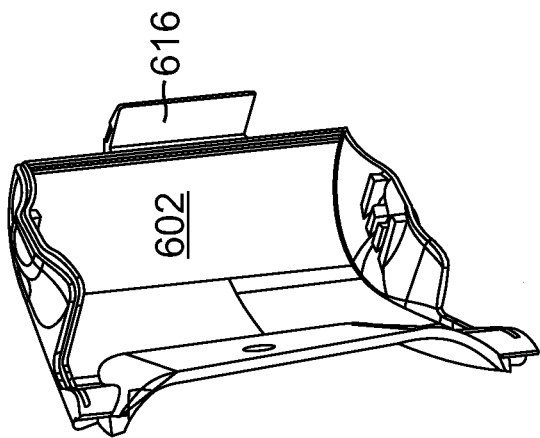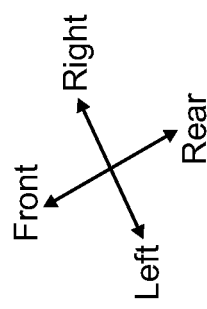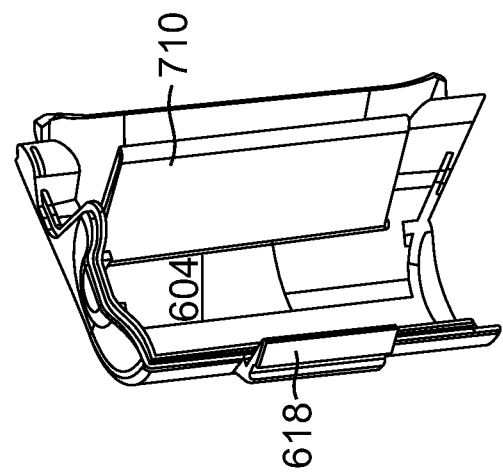
FIG. 7

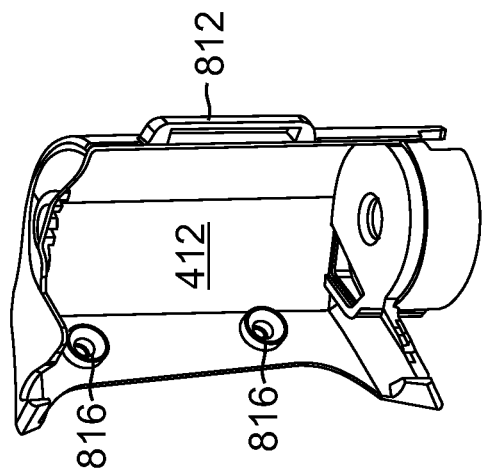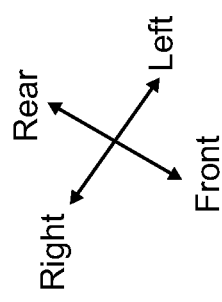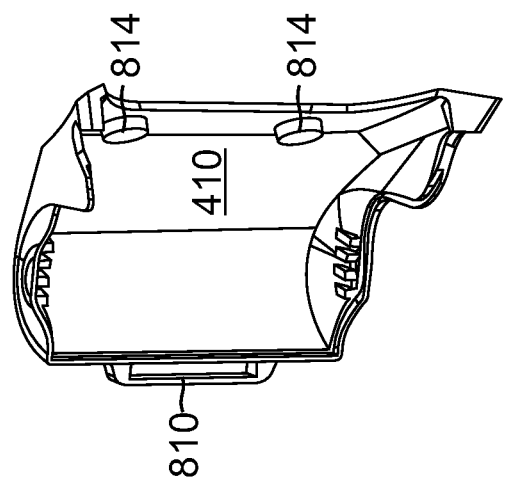
FIG. 8

ROLL-OFF FILM SYSTEM

CROSS-REFERENCE TO RELATED APPLICATION

This patent application claims the benefit of and priority to U.S. Provisional Patent Application No. 61/994,665, filed May 16, 2014 and entitled "Roll-Off Film System," which is hereby incorporated by reference in its entirety.

TECHNICAL FIELD

One or more embodiments relate generally to roll-off film systems and, more particularly, to roll-off film systems for sport goggles.

BACKGROUND

Sport goggles are worn by users for various sports or activities, such as motorsports, powersports, snowsports, watersports, biking, or the like, to protect users' eyes. A sport goggle may be installed with a roll-off film system to preserve a field of view on the lens of the sport goggle. In particular, the roll-off film system may stretch a section of a clear film across the lens of the sport goggle. When the section of the clear film is filled with dirt or debris from the sport activity, the roll-off film system may convey the used section of the clear film off the lens and a new section of the fill may be conveyed onto the lens to provide a clear field of view for the user. Nevertheless, dirt or mud may enter through an interface between the roll-off film system and the lens of the goggle and may reduce the field of view on the lens, which may render the roll-off film system ineffective. Further, dirt or mud may enter the canisters of the roll-off film system during the film conveying process which may interfere with the rolling mechanism of the roll-off film system. As such, there is a need for an improved roll-off film system that may address one or more of these shortcomings.

SUMMARY

Roll-off film systems and methods are provided in accordance with one or more embodiments that may be installed on goggle frames or adaptors to goggle frames to provide improved field of vision for users. In particular, film canisters of the roll-off film systems may include contact portions configured to seamlessly contact the goggle frame or the adaptor to the goggle frame. Further, the film canisters may include blade sections configured to remove mud or dirt from a used section of clear film when the used section is conveyed into the film canister to prevent excess mud or dirt from entering the film canister. The blade sections may also be configured to slant away from the field of view on the lens to allow the mud or dirt to fall away from the field of view on the lens to provide better field of view for the user.

In accordance with an embodiment, a roll-off film system may include a film dispensing canister configured to store and dispense a film and a film receiving canister configured to receive the film dispensed from the film dispensing canister. The film receiving canister may include a blade portion configured to cover the film when the film is conveyed into the film receiving canister.

In accordance with an embodiment, the film receiving canister is attached to a lens and a surface of the blade portion forms an obtuse angle with a surface of the lens. In accordance with an embodiment, the film receiving canister further may include an upper wing portion and a lower wing portion with the blade portion disposed between the upper and the lower wing portions. The upper wing portion and the lower wing portion may extend further upstream in a film conveying direction of the film than the blade portion.

In accordance with an embodiment, an edge of the blade portion is configured to slide on the film when the film is conveyed into the film receiving canister. An upper portion of the edge protrudes further upstream in a film conveying direction than a lower portion of the edge.

In accordance with an embodiment, a goggle assembly may include a lens, a lens frame configured to receive the lens, and a roll-off film system attached to the lens. The roll-off film system may include a film dispensing canister configured to store and dispense a film across a front surface of the lens in a film conveying direction and a film receiving canister configured to receive the film dispensed across the front surface of the lens from the film dispensing canister. The film receiving canister may include a blade portion configured to cover the film when the film is conveyed into the film receiving canister. In an embodiment, the lens frame is disposed in a front portion of a goggle frame. In another embodiment, the lens frame is an adaptor attachable to a goggle frame.

In accordance with an embodiment, a method includes conveying a film from a film dispensing canister across a front surface of a lens to a film receiving canister, and collecting debris on the film at a blade portion of the film receiving canister before the film is conveyed into the film receiving canister. The method also includes directing the debris collected on the blade portion away from a field of view of the lens by a slanting edge of the blade portion.

The scope of the invention is defined by the claims, which are incorporated into this Summary by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 4 shows an exposed view of the roll-off film system of FIG. 1, in accordance with an embodiment.

FIG. 6 shows a perspective front view of front casings, in accordance with an embodiment.

FIG. 7 shows a perspective rear view of the front casings of FIG. 6, in accordance with an embodiment.

FIG. 8 shows a perspective front view of rear casings, in accordance with an embodiment.

Embodiments of the invention and their advantages are best understood by referring to the detailed description that follows. It should be appreciated that like reference numerals are used to identify like elements illustrated in one or more of the Figures.

DETAILED DESCRIPTION

A roll-off film system configured to attach to a goggle frame or an adaptor to a goggle frame is disclosed in accordance with various embodiments. The roll-off film system may include a film dispensing canister configured to dispense a film across a goggle lens to a film receiving canister. In particular, the film receiving canister may include a blade portion configured to collect dirt or debris landed on the film before the film is conveyed into the film receiving canister. The blade portion may have an edge sloping away from a field of view of the goggle lens with respect to a film conveying direction, such that the dirt or debris collected on the blade section may be guided away from the field of view of the goggle lens to improve a user's view through the goggle lens. The film dispensing canister also may include a similar blade portion.

According to an embodiment, each of the film dispending canister and the film receiving canister may include an upper wing portion configured to extend over a mud flap of the goggle lens to prevent dirt or debris from entering an interface between the canister and the film. Each of the film dispending canister and the film receiving canister also may include a lower wing section configured to extend under a lower portion of the section of the film stretched across the goggle lens. Thus, the upper wing sections, the lower wing sections, and the blade portions of the film dispensing and receiving canisters, and the mud flap on the goggle lens effectively form a continuously barrier to prevent dirt or debris from entering between the film and the goggle lens.

In an embodiment, a front surface of the blade portion of the film receiving canister may form an obtuse angle with the goggle lens, such that the blade section may act as a shovel to pick up the dirt or debris landed on the film when the film is conveyed into the film receiving canister. Thus, the blade section may prevent or reduce the amount of dirt or debris on the film from entering the film receiving canister with the film.

Figure 1:
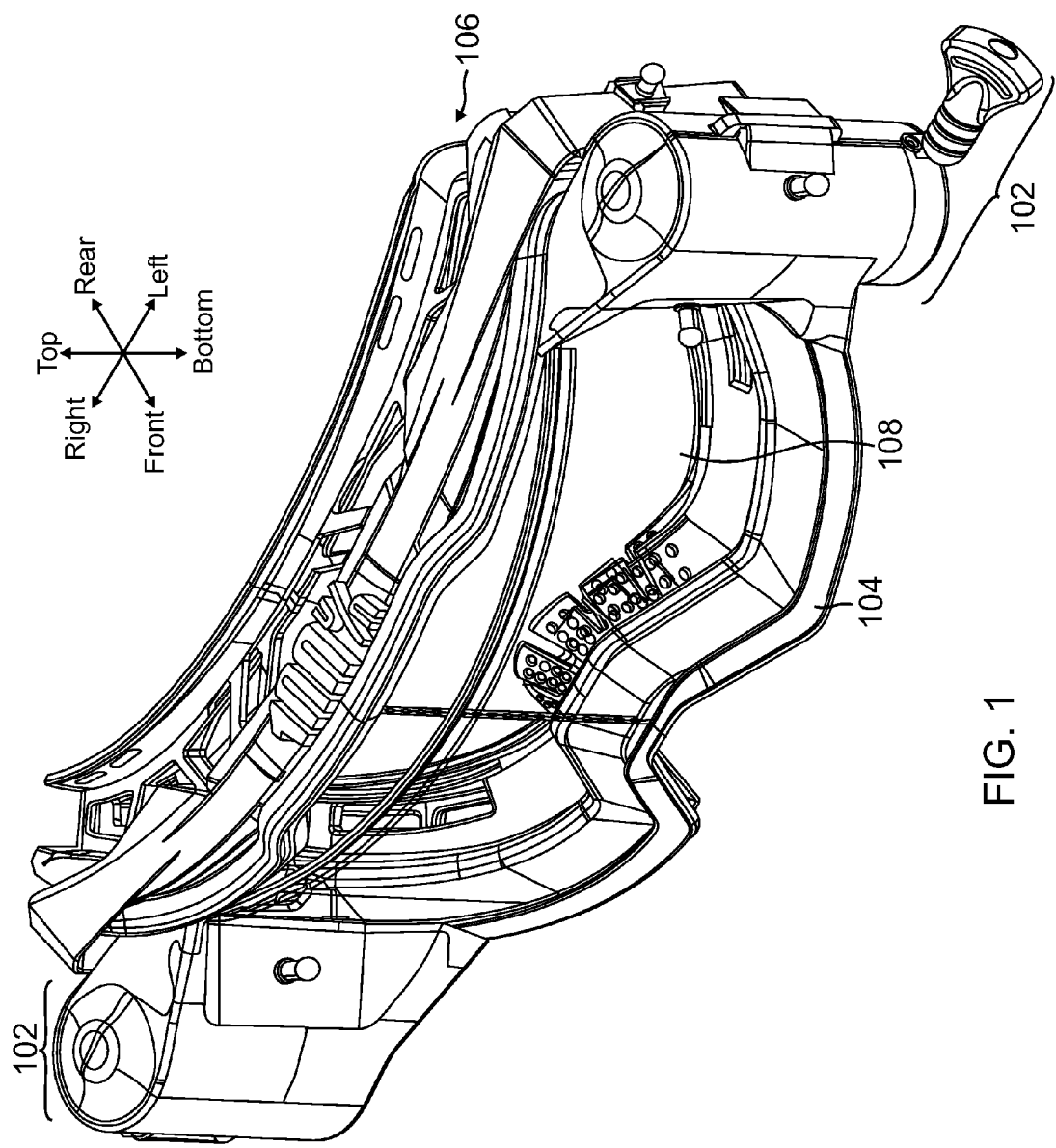
FIG. 1 shows a perspective front view of a roll-off film system installed on a goggle, in accordance with an embodiment.

FIG. 1 shows a perspective front view of a roll-off film system installed on a goggle, in accordance with an embodiment. As shown in FIG. 1, a goggle frame 106 may be installed with a roll-off film system 102. In particular, the roll-off film system 102 may be installed to the goggle frame 106 via an adaptor 108. The adaptor 108 may adapt the goggle frame 106 to use different goggle lenses and/or accessories. For example, the adaptor 108 may adapt the goggle frame 106 to use lenses of different sizes, shapes, curvatures, and the like. The adaptor 108 also may adapt the goggle frame 106 to use roll-off film systems of different film sizes.

The roll-off film system 102 may be attached to the lens 108, which is installed in the adaptor 104. The adaptor 104 may be attached to the goggle frame 106. In some embodiments, the lens 108 may be installed directly to the goggle frame 106, without the adaptor 104. Thus, the roll-off film system 102 may be installed on the goggle frame 106 without using the adaptor 104. The roll-off film system 102 may stretch a section of a film on the lens 108. When the section of the film becomes filled with dirt or debris, the used section of the film may be conveyed off the lens 108 and a new section of the film may replace the used section of the film to provide the user with clear field of view on the lens 108.

Figure 2:
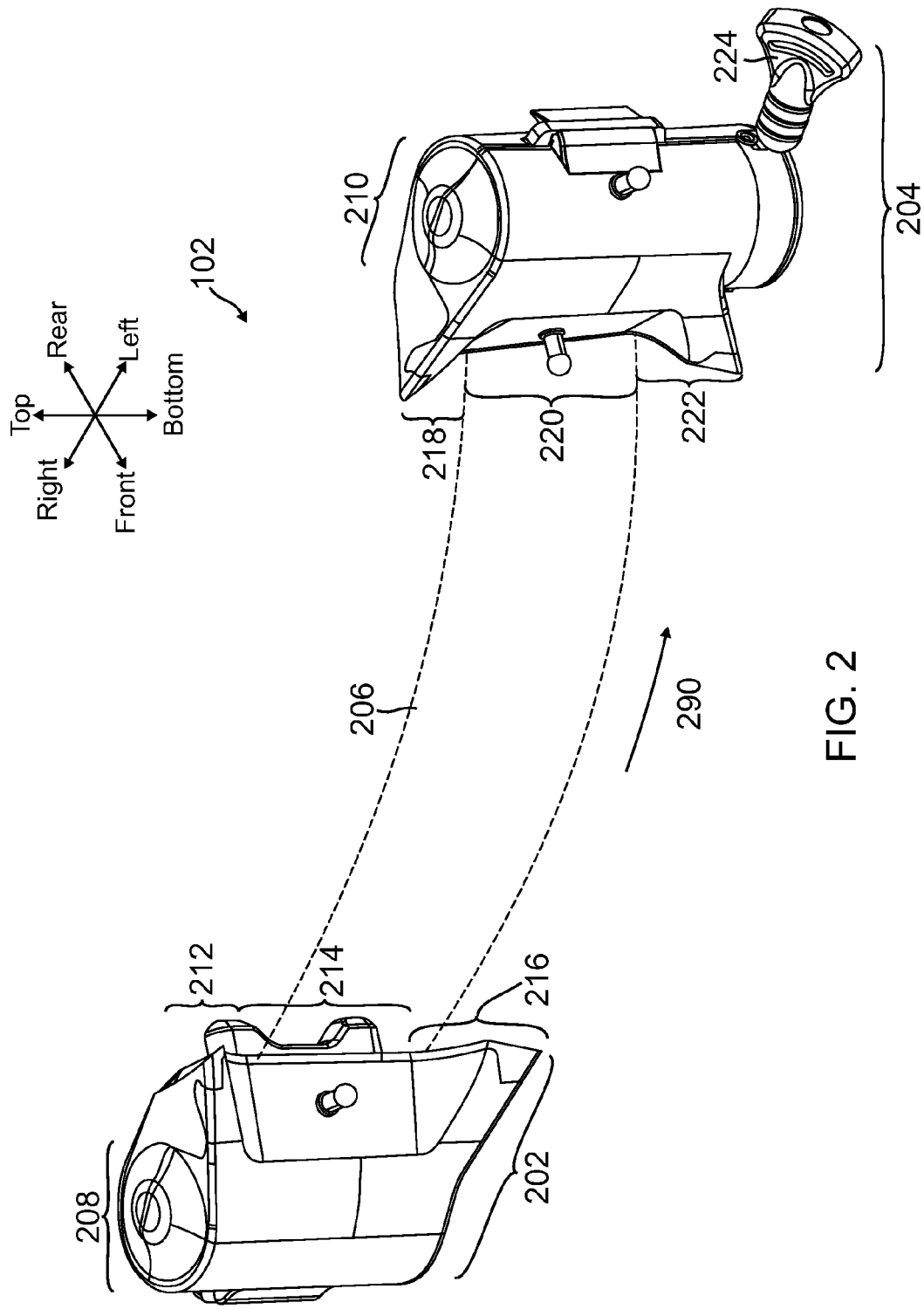
FIG. 2 shows a perspective front view of the roll-off film system of FIG. 1, in accordance with an embodiment.
Figure 3:
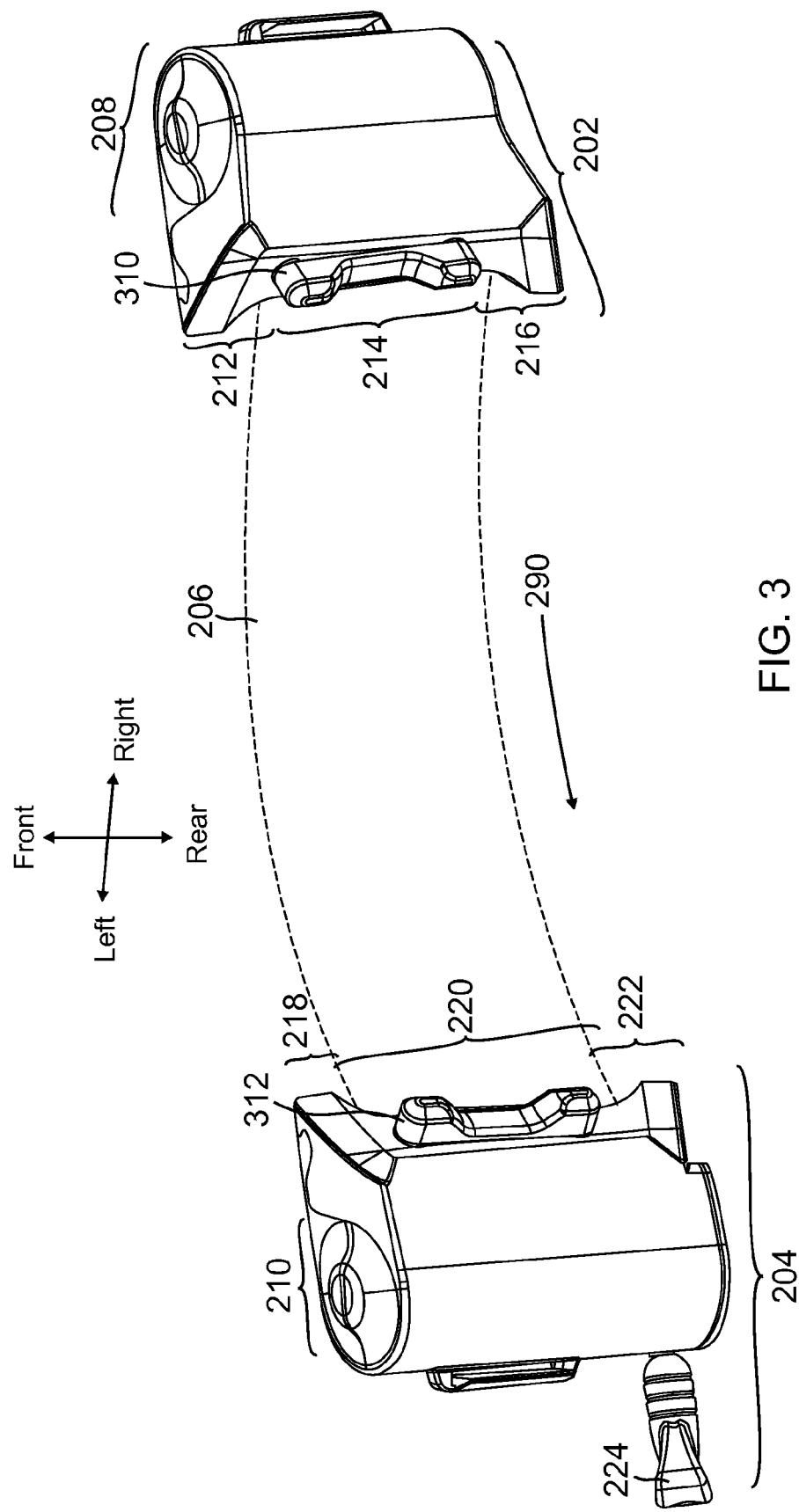
FIG. 3 shows a perspective rear view of the roll-off film system of FIG. 1, in accordance with an embodiment.

FIGS. 2 and 3 show perspective front and rear views of the roll-off film system of FIG. 1, in accordance with an embodiment. As shown in FIGS. 2 and 3, the roll-off film system 102 may include a film dispensing canister 202 and a film receiving canister 204. The film dispensing canister 202 may dispense a section of a film 206 across the lens 108 toward the film receiving canister 204. The film receiving canister 204 may receive the film 206 from the film dispensing canister 202. The film receiving canister 204 may include a pull cord handle 224, which is attached to an end of a string configured to drive a conveyance of the film from the film dispensing canister 202 to the film receiving canister 204 in a film conveying direction 290. For example, when the section of the film 206 resting on the lens 108 becomes filled with dirt or debris, a user may pull the pull cord handle 224 to roll the used section of the film 206 into the film receiving canister 204 and to convey a new section of the film 206 onto the lens 108 to provide clear field of view on the lens 108.

The film dispensing canister 202 may include a film storage portion 208 within which the film 206 may be stored. The film dispensing canister 202 also may include an upper wing portion 212, a lower wing portion 216, and a blade portion 214 disposed between the upper wing portion 212 and the lower wing portion 216. The upper wing portion 212 and the lower wing portion 216 may protrude further downstream in the film conveying direction 290 than the blade portion 214. The film 206 may exit the film dispensing canister 202 through an opening at the blade portion 214.

The film receiving canister 204 may include a film storage portion 210 within which the film 206 received from the film dispensing canister 202 may be stored. The film receiving canister 204 also may include an upper wing portion 218, a lower wing portion 222 and, a blade portion 220 disposed between the upper wing portion 218 and the lower wing portion 222. The upper wing portion 218 and the lower wing portion 222 may protrude further upstream in the film conveying direction 290 than the blade portion 220. The film 206 may be conveyed into the film receiving canister 204 through an opening at the blade portion 220. As shown in FIG. 3, the film dispensing canister 202 may include a lens attachment mechanism 310 configured to attach the film dispensing canister 202 to the lens 108. Similarly, the film receiving canister 204 may include a lens attachment mechanism 312 configured to attach the film receiving canister 204 to the lens 108.

FIG. 4 shows an exposed view of the roll-off film system of FIG. 1, in accordance with an embodiment. The film dispensing canister 202 may include a film dispensing axle 402 disposed in the film storage portion 208. Unused sections of the film 206 may be wound around the film dispensing axle 402 into a roll. The film dispensing axle 402 may rotate to unwound particular sections of the film 206 as the particular sections of the film 206 is dispensed from the film dispensing canister 202. The film receiving canister 204 may include a film receiving axle 404 disposed in the film storage portion 210. Used sections of the film 206 may be wound around the film receiving axle 404 into a roll. The film receiving axle 404 may be driven by a pull cord to rotate and to wind the film 206 into the film receiving canister 204. A pull cord housing 406 may be disposed under the film receiving axle 404.

Figure 5:
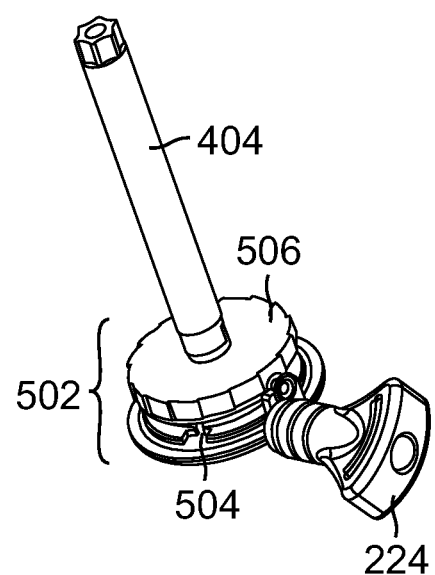
FIG. 5 shows a perspective view a ratchet mechanism, in accordance with an embodiment.

As shown in FIG. 5, a ratchet mechanism assembly 502 may be provided within the pull cord housing 406. The ratchet mechanism assembly 502 may include a ratchet 506 configured to transfer a pull force from a pull cord to the film receiving axle 402. A pull cord (not shown) connected to the pull cord handle 224 may be wound and stored under the ratchet 506 in the pull cord housing 406. When the user 224 pulls on the pull cord handle 224, the pull cord is unwound which may cause the ratchet 506 and the film receiving axle 404 to rotate. As the film receiving axle 404 rotates, additional sections of the film 206 may be wound onto the film receiving axle 404. This may cause a conveying motion along the film 206 which pulls a new section of the film 206 from the film dispensing canister 202 onto the lens 108. The ratchet mechanism assembly 502 may include a pull cord retracting mechanism (not shown) configured to automatically rewind the cord into the pull cord housing 406 after the cord is pulled. Thus, the cord may be ready to be pulled for conveying the next section of the film 206 onto the lens 108.

The film dispensing canister 202 may be formed by a front casing 602, as shown in FIG. 6, coupled to a rear casing 410, as shown in FIG. 4. The front casing 602 and the rear casing 410 may form a cavity for storing unused sections of the film 206. Similarly, the film receiving canister 204 may be formed by a front casing 604, as shown in FIG. 6, coupled to a rear casing 412, as shown in FIG. 4. The front casing 604 and the rear casing 412 may form a cavity for storing used sections of the film 206. The casings 602, 410, 604, and 412 may be formed with certain plastic resin, such as polycarbonate. In other embodiments, the casings may be formed with metal, synthetic material, bio-material, or the like. The casings may be formed by injection molding. In other embodiments, the casings may be formed by three-dimensional (3D) printing.

FIGS. 6 and 7 show perspective front and rear views of the front casings, in accordance with an embodiment. As shown in FIG. 6, the front casing 602 of the film dispensing canister 202 may include a coupling mechanism 616 configured to couple the front casing 602 to the rear casing 410. Similarly, the front casing 604 of the film receiving canister 204 may include a coupling mechanism 618 configured to fix the front casing 604 to the rear casing 412. Coupling mechanisms 616 and 618 each may include a deformable hook.

The upper wing portion 212 of the front casing 602 may include a triangular shaped surface 610. The blade portion 214 of the front casing 602 may include a sloping surface 606. The lower wing portion 216 of the front casing 602 may include a triangular shaped surface 614. The triangular shaped surface 610 may curve from facing down at a top portion thereof to facing a horizontal direction at a lower portion thereof. The triangular shaped surface 614 may curve from facing the horizontal direction at a top portion thereof to facing up at a lower portion thereof. The triangular shaped surface 610, the sloping surface 606, and the triangular shaped surface 614 may form a continuous, broad U-shaped surface. A tear-off pin 620 may be disposed on the sloping surface 606 at which a user may pull to separate the front casing 602 from the rear casing 410.

The upper wing portion 218 of the front casing 604 may include a triangular shaped surface 612. The blade portion 220 of the front casing 604 may include a sloping surface 608. The lower wing portion 222 of the front casing 604 may include a triangular shaped surface 616. The triangular shaped surface 612 may curve from facing down at a top portion thereof to facing a horizontal direction at a lower portion thereof. The triangular shaped surface 616 may curve from facing the horizontal direction at a top portion thereof to facing up at a lower portion thereof. The triangular shaped surface 612, the sloping surface 608, and the triangular shaped surface 616 may form a continuous, broad U-shaped surface. Tear-off pins 622 and 624 may be disposed on front casing 604 at which a user may pull to separate the front casing 604 from the rear casing 412. Referring to FIG. 7, a protruding plate 710 may be disposed in front casing 604. The protruding plate 710 may be positioned in such a manner as to guide the film 206 that is being conveyed into the film receiving canister 204. In some embodiments, the protruding plate 710 may provide additional tension to the film 206 to hold the film 206 tightly on the lens 108.

Figure 9:
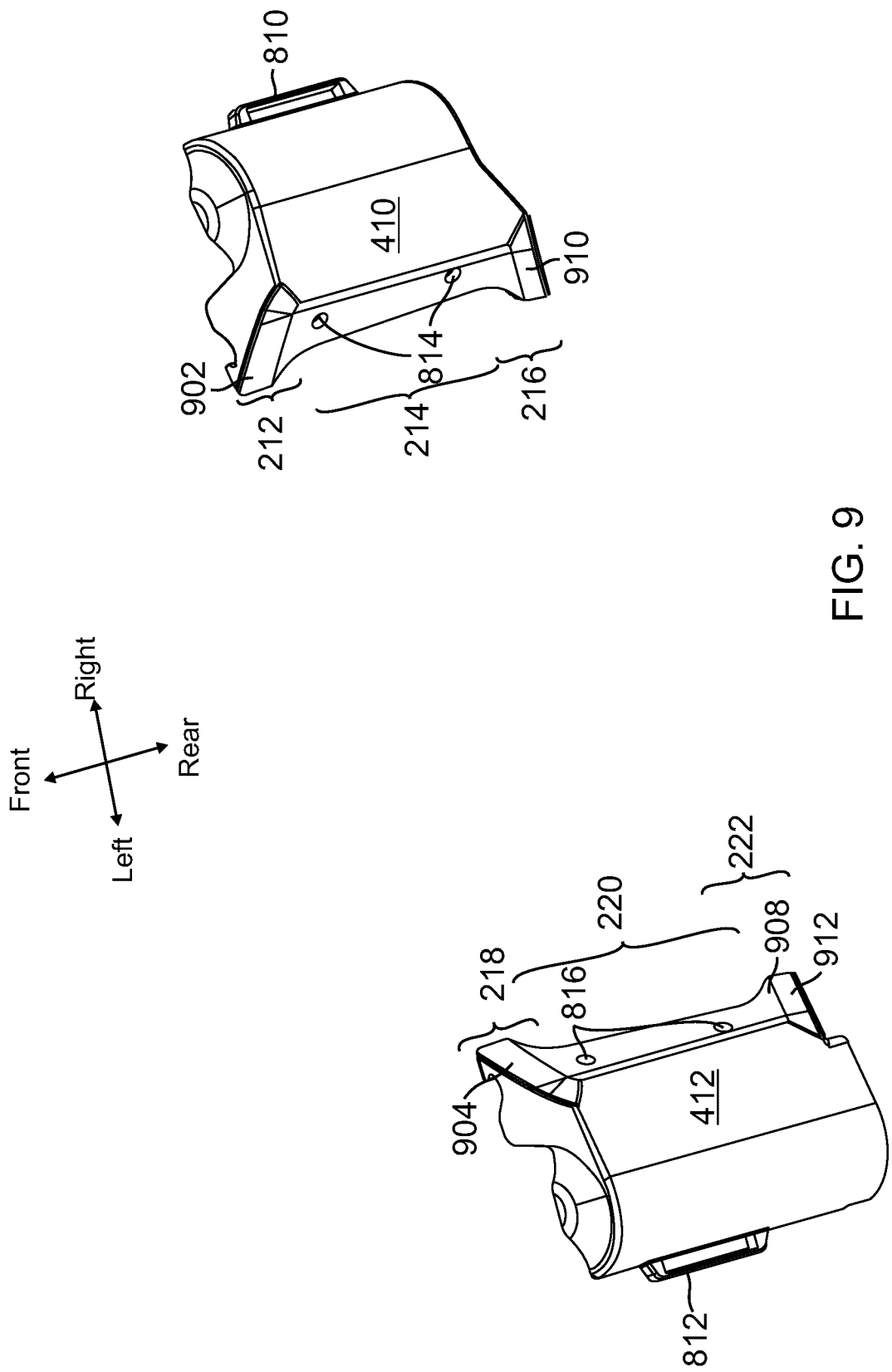
FIG. 9 shows a perspective rear view of the rear casings of FIG. 8, in accordance with an embodiment.

FIGS. 8 and 9 show perspective front and rear views of rear casings, in accordance with an embodiment. As shown in FIG. 8, rear casing 410 may include a side loop 810 configured to receive and retain the coupling mechanism 616 of front casing 602. For example, the deformable hook of the coupling mechanism 616 may be inserted through the side loop 810 to couple the front casing 602 to the rear casing 410. The deformable hook may hook onto the loop 810 to retain the front casing 602 to the rear casing 410. The rear casing 410 also may include two lens attachment openings 814 through which the lens attachment mechanism 310 may be inserted.

Similarly, rear casing 412 may include a side loop 812 configured to receive and retain the coupling mechanism 618 of front casing 604. For example, the deformable hook of the coupling mechanism 618 may be inserted through the side loop 812 to couple the front casing 604 to the rear casing 412. The deformable hook may hook onto the loop 812 to retain the front casing 604 to the rear casing 412. The rear casing 412 also may include two lens attachment openings 816 through which the lens attachment mechanism 312 may be inserted.

Referring to FIG. 9, the upper wing portion 212 of the rear casing 410 may include an upper frame contacting surface 902. The upper frame contacting surface 902 may have a contour substantially conforming to the area of the goggle frame 106 or adaptor frame 104 where the rear casing 410 contacts. The blade portion 214 of the rear casing 410 may include a lens contacting surface 906. Two lens attachment openings 814 may form through the lens contacting surface 906. The lens contacting surface 906 may have a contour substantially conforming to the area of the lens 108 where the rear casing 410 contacts. The lower wing portion 216 of the rear casing 410 may include a lower frame contacting surface 910. The lower frame contacting surface 910 may have a contour substantially conforming to the area of the goggle frame 106 or adaptor frame 104 where the rear casing 410 contacts.

The upper wing portion 218 of the rear casing 412 may include an upper frame contacting surface 904. The upper frame contacting surface 904 may have a contour substantially conforming to the area of the goggle frame 106 or adaptor frame 104 where the rear casing 412 contacts. The blade portion 220 of the rear casing 412 may include a lens contacting surface 908. Two lens attachment openings 816 may form through the lens contacting surface 908. The lens contacting surface 908 may have a contour substantially conforming to the area of the lens 108 where the rear casing 412 contacts. The lower wing portion 222 of the rear casing 412 may include a lower frame contacting surface 912. The lower frame contacting surface 912 may have a contour substantially conforming to the area of the goggle frame 106 or adaptor frame 104 where the rear casing 412 contacts.

Figure 10:
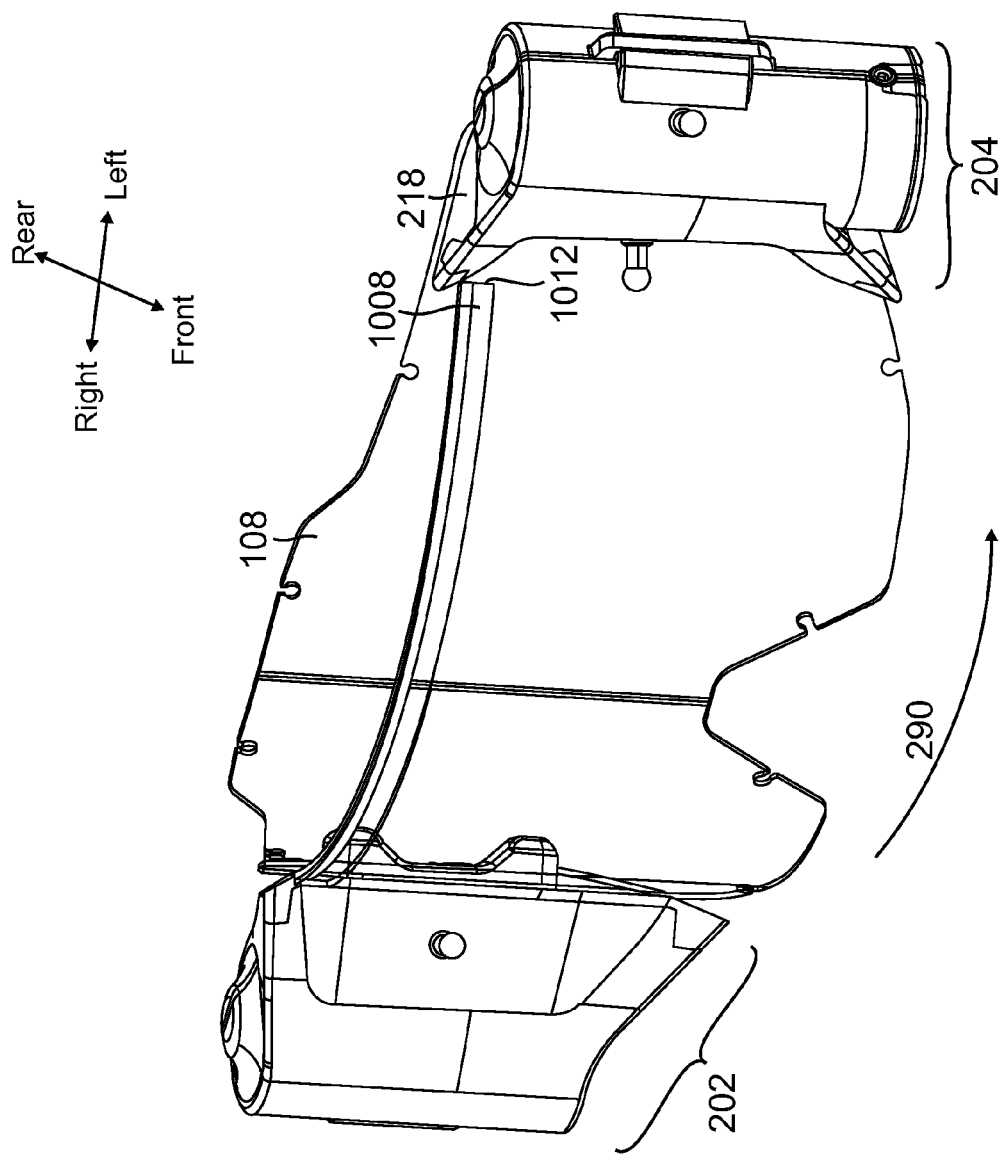
FIG. 10 shows a perspective front view of a roll-off film system attached to a lens, in accordance with an embodiment.
Figure 11:
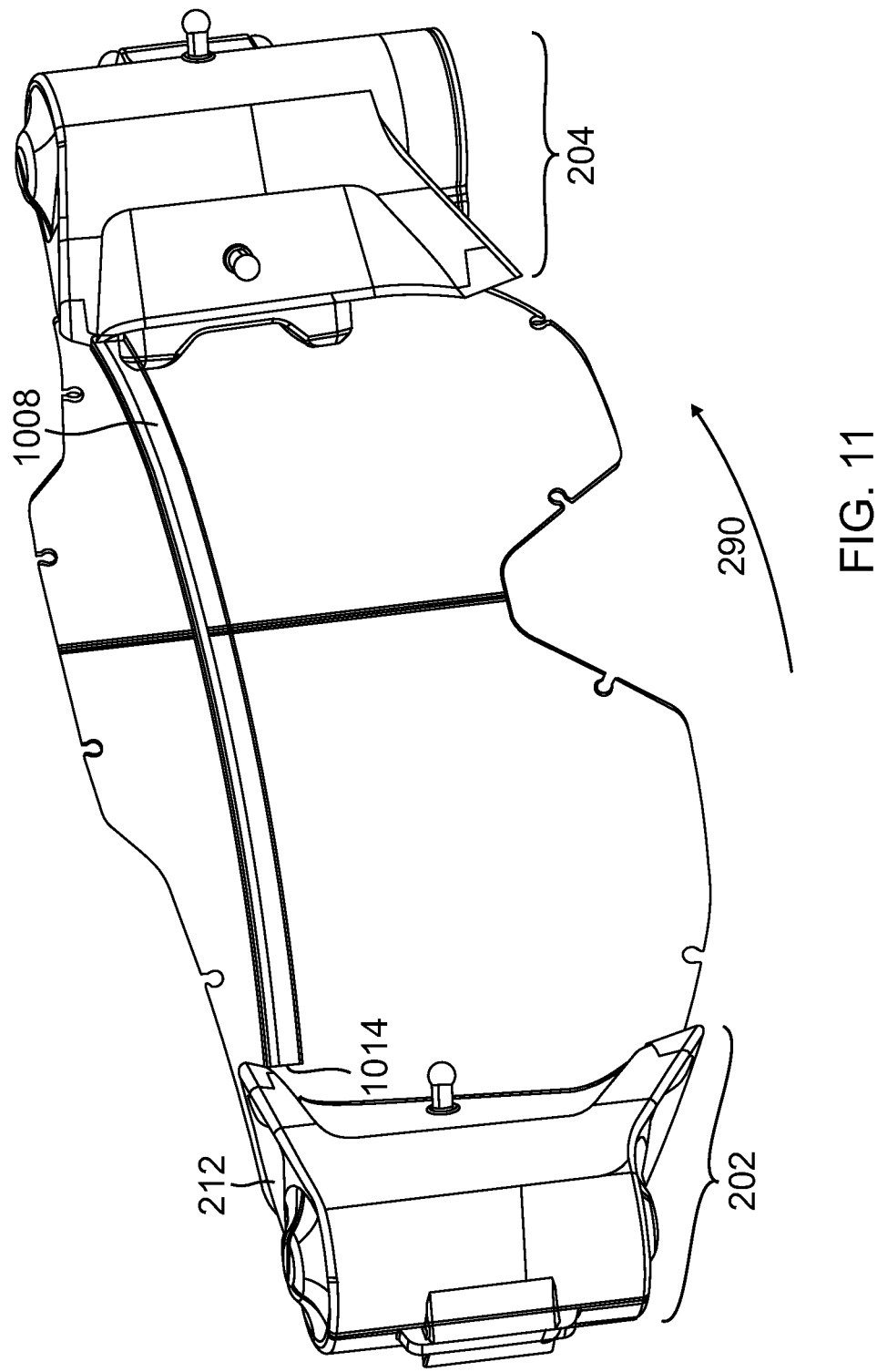
FIG. 11 shows another perspective front view of the roll-off film system attached to the lens of FIG. 10, in accordance with an embodiment.

FIGS. 10 and 11 show perspective front views of a roll-off film system attached to a lens, in accordance with an embodiment. Lens 108 may include a mud flap 1008 disposed on and across the front-top portion of the lens 108. The mud flap 1008 may prevent dirt or mud from dripping down and entering between the film 206 and the front surface of the lens 108. As shown in FIG. 10, the upper wing portion 218 of the film receiving canister 204 may extend over the right end portion of the mud flap 1008. Thus, the upper wing portion 218 may prevent mud from entering between the mud flap 1008 and the film receiving canister 204 and dripping downward into the film 206. Similarly, as shown in FIG. 11, the upper wing portion 212 of the film dispensing canister 202 may extend over the left end portion of the mud flap 1008. Thus, the upper wing portion 212 may prevent mud from entering between the mud flap 1008 and the film dispensing canister 202 and dripping downward into the film 206. Accordingly, the upper wing portions 212, and 218, the blade portions 214 and 220, the lower wing portions 216 and 222, and the mud flap 1008 may form a barrier surrounding the section of film 206 covering the lens 108 to prevent mud or dirt from entering between the film 206 and the lens 108.

Figure 12:
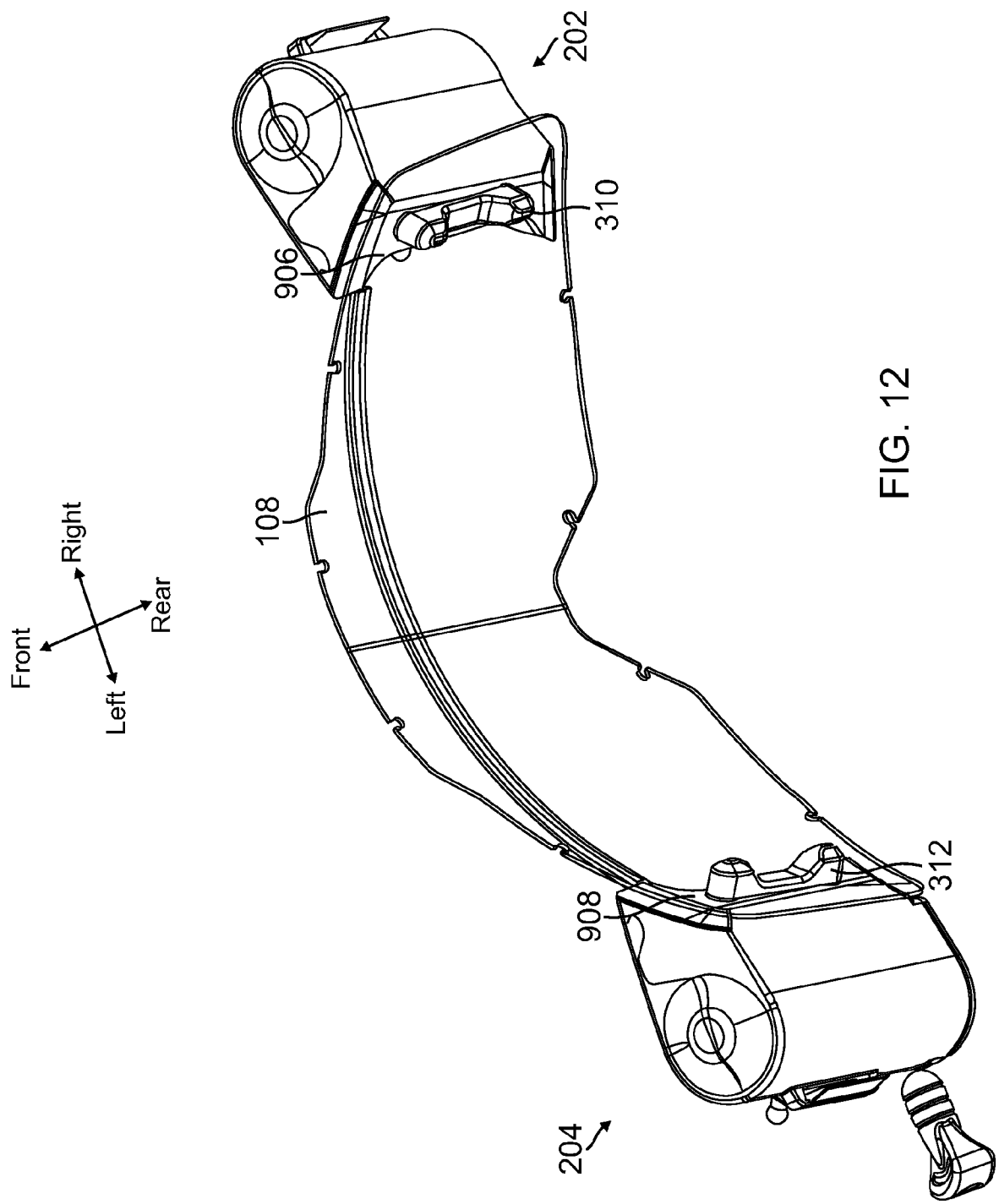
FIG. 12 shows a perspective rear view of the roll-off film system attached to the lens of FIG. 10, in accordance with an embodiment.

FIG. 12 shows a perspective rear view of the roll-off film system attached to the lens of FIG. 10, in accordance with an embodiment. Film dispensing canister 202 may be attached to the lens 108 by lens attachment mechanism 310. The lens attachment mechanism 310 may include a strap with pins on both ends of the strap. The pins may be inserted through two openings in the lens 108 to fasten the strap through the openings to the film dispensing canister 202. The lens contacting surface 906 of the film dispensing canister 202 may have a contour substantially conforming to that of the lens 108 to seamlessly contact the lens 108. Similarly, film receiving canister 204 may be attached to the lens 108 by lens attachment mechanism 312. The lens attachment mechanism 312 may include a strap with pins on both ends of the strap. The pins may be inserted through two openings in the lens 108 to fasten the strap through the openings to the film receiving canister 204. The lens contacting surface 908 of the film receiving canister 204 may have a contour substantially conforming to that of the lens 108 to seamlessly contact the lens 108.

Figure 13:
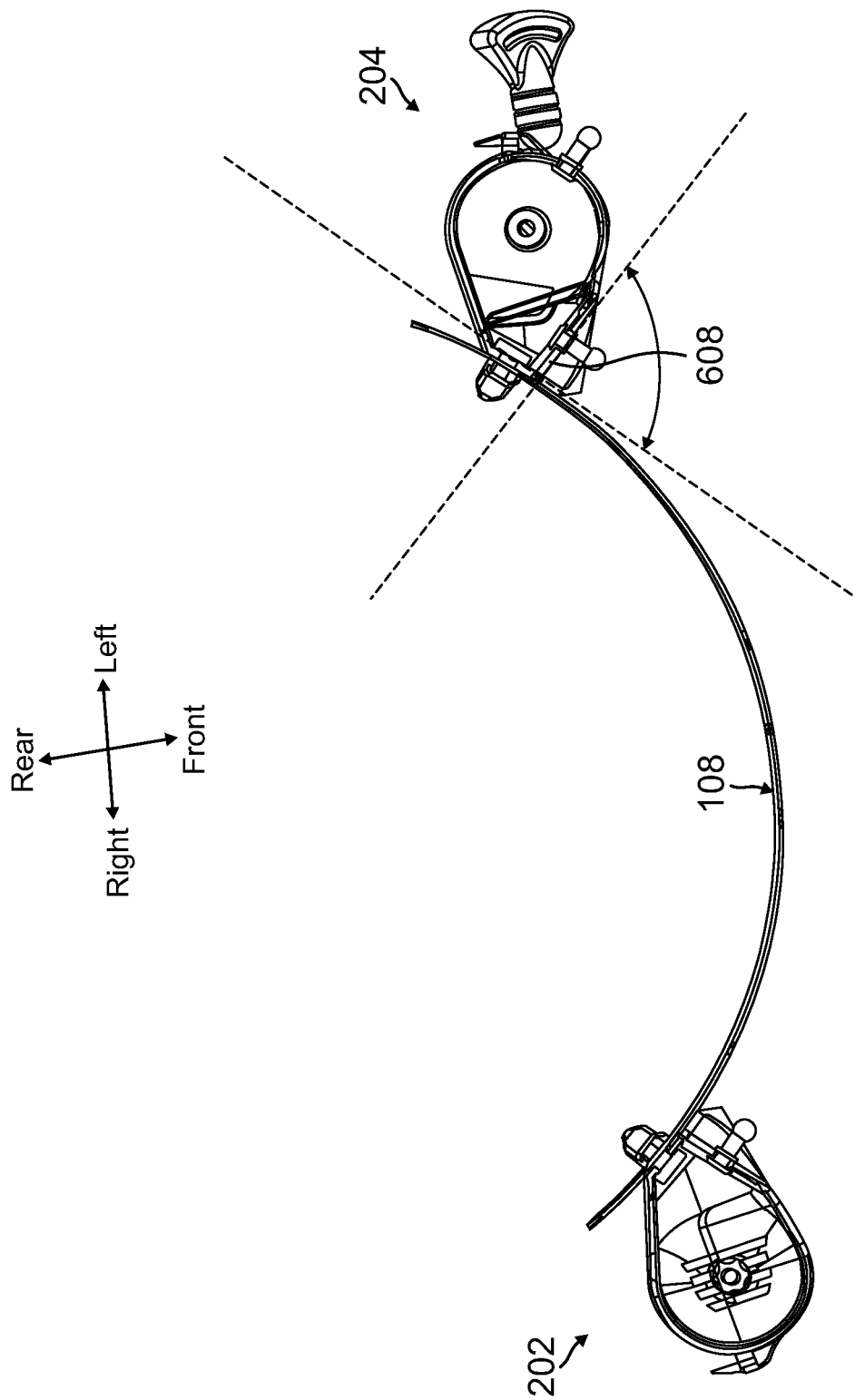
FIG. 13 shows a perspective top view of the roll-off film system attached to the lens of FIG. 10, in accordance with an embodiment.

Referring to FIG. 13, the sloping surface 608 of the blade portion 220 of the film receiving canister 204 may form an obtuse angle with the front surface of the lens 108. As such, dirt or mud collected on the film 206 may be removed and collected on the sloping surface 608 of the blade portion 220 when the film 206 is conveyed through the blade portion 220 into the film receiving canister 204. This may effectively prevent excess amount of mud or dirt from entering into the film receiving canister 204 and may prolong the use of the roll-off film system 102.

Figure 14:
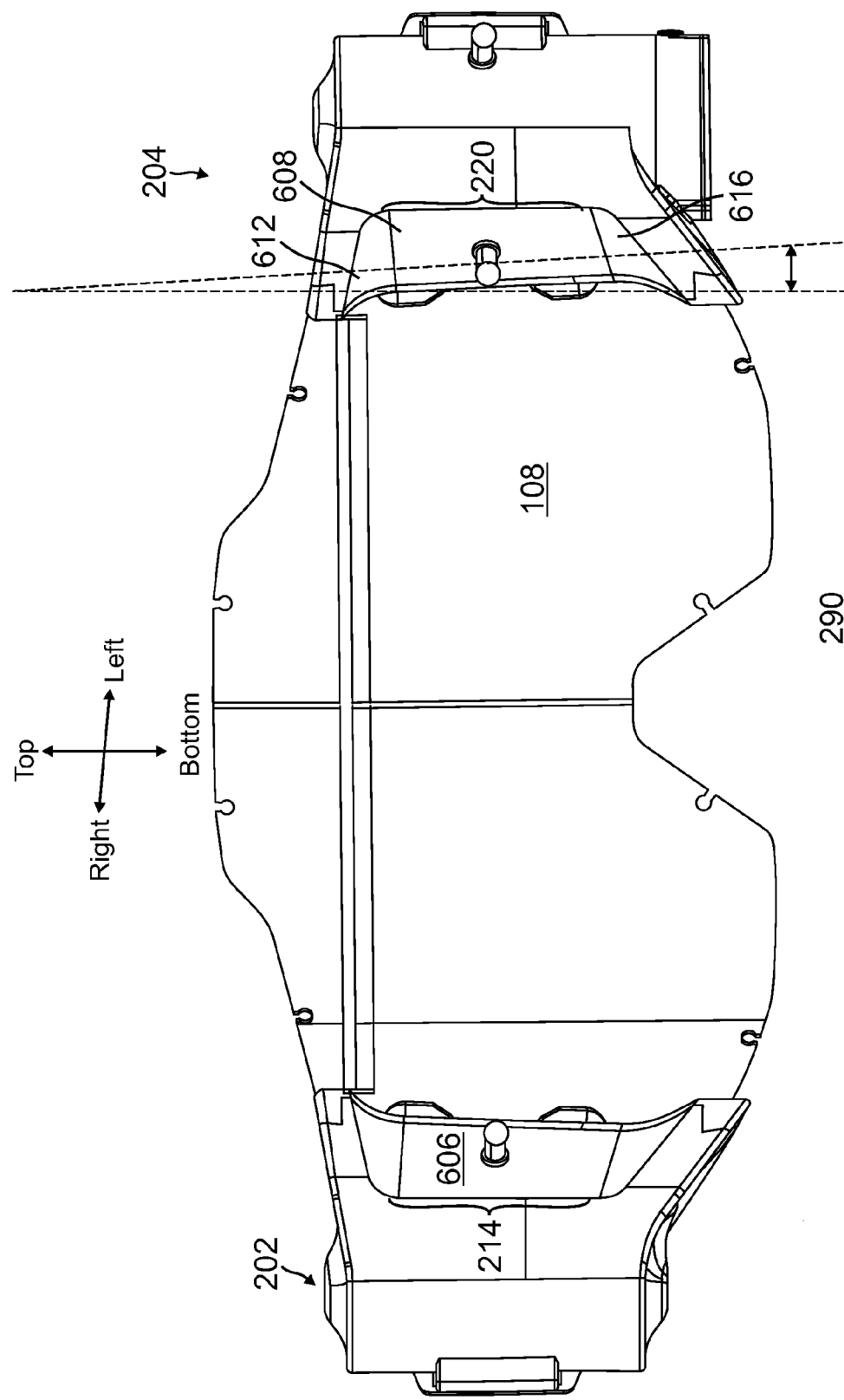
FIG. 14 shows a front view of the roll-off film system attached to the lens of FIG. 10, in accordance with an embodiment.

Referring to FIG. 14, an edge of the sloping surface 608 of the blade portion 220 of the film receiving canister 204 may slant away from the field of view at the lower portion of the edge. Thus, the edge may form an angle with a vertical reference line, such that the upper portion of the edge of the sloping surface 608 may be positioned more upstream in the film conveying direction 290 than the lower portion of the edge of the sloping surface 608. Thus, mud or debris collected on the sloping surface 608 may fall down and be directed away from the field of view, instead of remaining on the sloping surface 608. Similarly, an edge of the sloping surface 606 of the blade portion 214 of the film dispensing canister may slant away from the field of view at the lower portion of the edge. For example, the upper portion of the edge of the sloping surface 606 may be positioned more downstream in the film conveying direction 290 than the lower portion of the edge of the sloping surface 606. Thus, mud or debris collected on the sloping surface 606 may fall down and away from the field of view.

Figure 15:
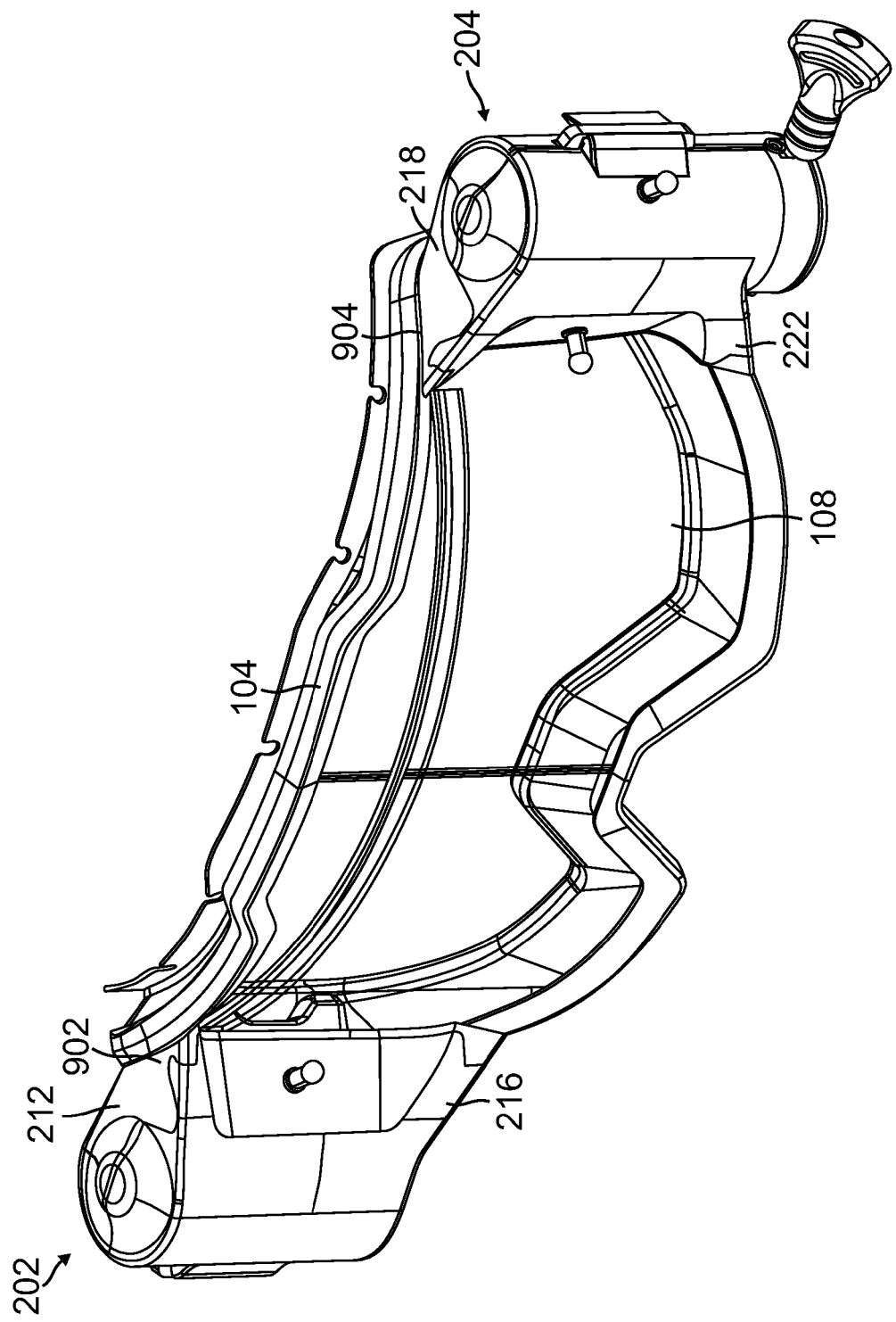
FIG. 15 shows a perspective front view of a roll-off film system attached to an adaptor, in accordance with an embodiment.

FIG. 15 shows a perspective front view of a roll-off film system attached to an adaptor, in accordance with an embodiment. The lens 108 may be installed in the adaptor 104 and the roll-off film system 102 may be installed on the lens 108. As shown in FIG. 15, the frame contacting surface 902 of the upper wing portion 212 may have a contour conforming to that of the adaptor 104 to seamlessly contact the adaptor 104. Similarly, the frame contacting surface 904 of the upper wing portion 218 may have a contour conforming to that of the adaptor 104 to seamlessly contact the adaptor 104. Thus, mud or debris may be prevented from entering through the interface between the roll-off film system 102 and the adaptor 104.

Figure 16:
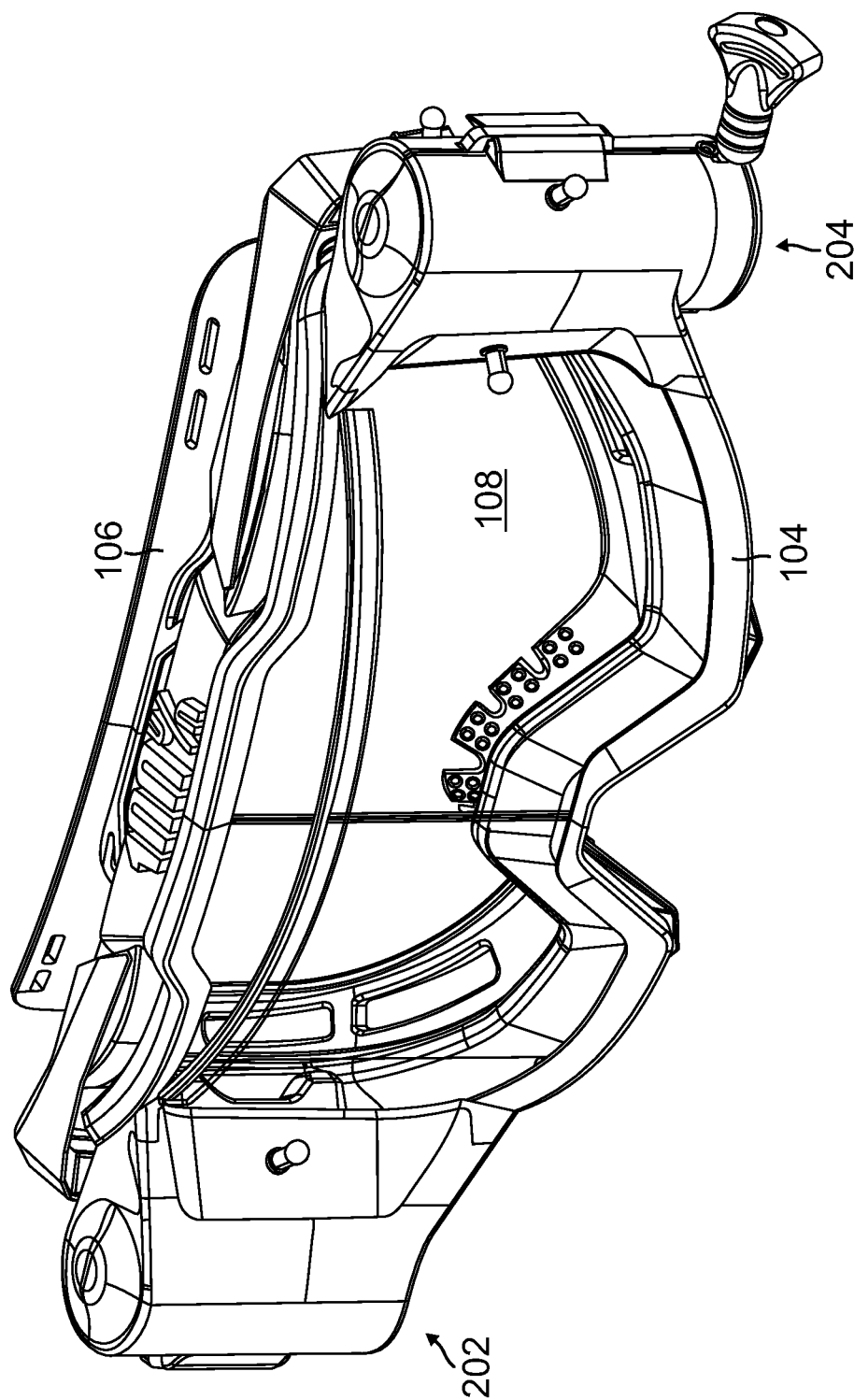
FIG. 16 shows a perspective front view of a roll-off film system attached to an adaptor and a goggle frame, in accordance with an embodiment.

FIG. 16 shows a perspective front view of a roll-off film system attached to an adaptor and a goggle frame, in accordance with an embodiment. The adaptor 104 installed with the roll-off film system 102 may be installed into a goggle frame 106. The adaptor 104 may adapt the goggle frame 106 to use various types of lenses and/or roll-off film systems. For example, the adaptor 104 may adapt the goggle frame 106 to use roll-off film systems of different film sizes, 35 mm film of 40 mm film.

Figure 17:
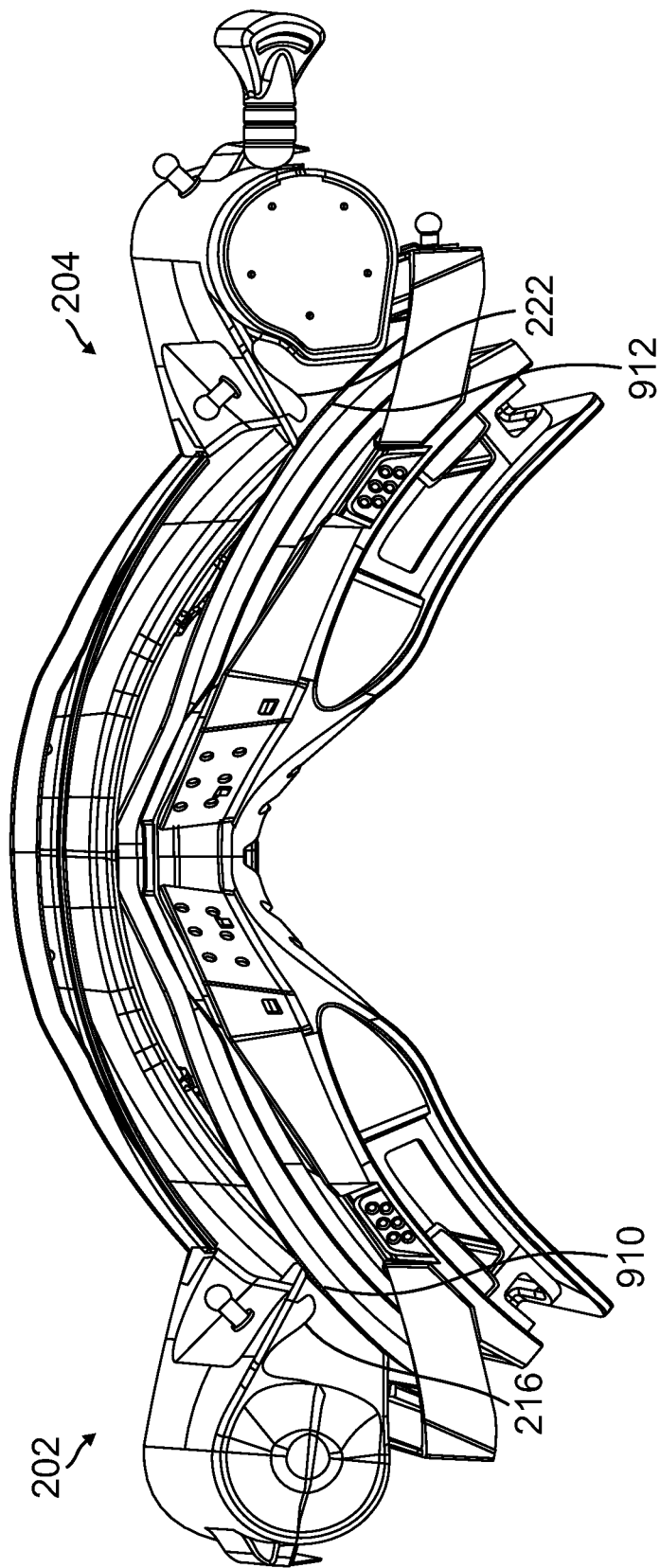
FIG. 17 shows a perspective bottom view of the roll-off film system attached to the adaptor and the goggle frame of FIG. 16, in accordance with an embodiment.

As shown in FIG. 17, the frame contacting surface 910 of the lower wing portion 216 may have a contour conforming to that of the adaptor 104 to seamless contact the adaptor 104. Similarly, the frame contacting surface 912 of the lower wing portion 222 may have a contour conforming to that of the adaptor 104 to seamless contact the adaptor 104. Thus, mud or debris may be prevented from entering through the interface between the roll-off film system 102 and the adaptor 104.

In some embodiments, the roll-off film system 102 may be installed onto the goggle frame 106 without using the adaptor 104. For example, the lens 108 may be installed onto the goggle frame 106 and the adaptor 104 may be attached to the lens 108. The frame contacting surfaces 902, 904, 910, and 912 may respectively conform to the contours of the goggle frame 106 to provide seamless contact between the canisters 202 and 204 and the goggle frame 106 to prevent mud or debris intrusion.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected is:

1. A roll-off film system comprising:
   a film dispensing canister configured to store and dispense a film;
   a film receiving canister configured to receive the film dispensed from the film dispensing canister, the film receiving canister comprising:
      a blade portion configured to cover the film when the film is conveyed into the film receiving canister; and
      an upper wing portion and a lower wing portion with the blade portion disposed between the upper and the lower wing portions, wherein an upper triangular surface of the upper wing portion, a sloping surface of the blade portion, and a lower triangular surface of the lower wing portion form a continuous surface configured to collect debris from the film,
      wherein the upper triangular surface is provided at a bottom side of the upper wing portion and the lower triangular surface is provided at a top side of the lower wing portion, and
      wherein an upper portion of the upper triangular surface is curved to face toward the lower triangular surface and a lower portion of the lower triangular surface is curved to face toward the upper triangular surface, such that the continuous surface has a broad, U-shape.

2. The roll-off film system of claim 1,
   wherein the film receiving canister is configured to attach to a lens, and
   wherein the sloping surface of the blade portion forms an obtuse angle with a surface of the lens to collect debris on the sloping surface when the film is conveyed into the film receiving canister.

3. The roll-off film system of claim 1, wherein the upper wing portion and the lower wing portion extend further upstream in a film conveying direction of the film than the blade portion.

4. The roll-off film system of claim 3, wherein the blade portion comprises a lens contacting surface configured to contact a front surface of a lens when the film receiving canister is attached to the lens.

5. The roll-off film system of claim 4,
   wherein the lens comprises a mud flap extending on an upper portion of the front surface along the film conveying direction from the film dispensing canister to the film receiving canister, and
   wherein the upper wing portion is configured to extend over a downstream end of the mud flap with respect to the film conveying direction.

6. The roll-off film system of claim 4, wherein the film receiving canister further comprises an attachment mechanism disposed on the lens contacting surface and configured to attach the film receiving canister to the lens.

7. The roll-off film system of claim 4,
   wherein the lens is received in a lens frame,
   wherein the upper wing portion of the film receiving canister further comprises a frame contacting surface configured to contact an upper portion the lens frame at a downstream end with respect to the film conveying direction, and
   wherein the frame contacting surface has a contour following a contour of the upper-downstream portion of the lens frame.

8. The roll-off film system of claim 1, wherein an edge of the sloping surface of the blade portion is configured to slide on the film when the film is conveyed into the film receiving canister, and wherein a pull-off pin is provided on the sloping surface.

9. The roll-off film system of claim 8, wherein an upper portion of the edge protrudes further upstream in a film conveying direction than a lower portion of the edge, such that the edge is slanted away from a field of view of the film at the lower portion of the edge to direct debris collected on the sloping surface away from the field of view.

10. A goggle assembly comprising:
    a lens;
    a lens frame configured to receive the lens;
    a roll-off film system attached to the lens, the roll-off film system comprising:
       a film dispensing canister configured to store and dispense a film across a front surface of the lens in a film conveying direction;
       a film receiving canister configured to receive the film dispensed across the front surface of the lens from the film dispensing canister, the film receiving canister comprising:
          a blade portion configured to cover the film when the film is conveyed into the film receiving canister; and
          an upper wing portion and a lower wing portion with the blade portion disposed between the upper and the lower wing portions, wherein an upper triangular surface of the upper wing portion, a sloping surface of the blade portion, and a lower triangular surface of the lower wing portion form a continuous surface configured to collect debris from the film;
       wherein the upper triangular surface is provided at a bottom side of the upper wing portion and the lower triangular surface is provided at a top side of the lower wing portion, and
       wherein an upper portion of the upper triangular surface is curved to face toward the lower triangular surface and a lower portion of the lower triangular surface is curved to face toward the upper triangular surface, such that the continuous surface has a broad, U-shape.

11. The goggle assembly of claim 10, wherein a surface of the blade portion forms an obtuse angle with the front surface of the lens.

12. The goggle assembly of claim 10,
    wherein the upper wing portion and the lower wing portion extend further upstream in a film conveying direction of the film than the blade portion.

13. The goggle assembly of claim 12,
    wherein the lens comprises a mud flap extending on an upper portion of the front surface along the film conveying direction, and
    wherein the upper wing portion is configured to extend over a downstream end of the mud flap with respect to the film conveying direction.

14. The goggle assembly of claim 12,
    wherein the upper wing portion of the film receiving canister further comprises a frame contacting surface configured to contact an upper portion the lens frame at a downstream end with respect to the film conveying direction, and wherein the frame contacting surface has a contour following a contour of the upper-downstream portion of the lens frame.

15. The goggle assembly of claim 10, wherein an edge of the blade portion is configured to slide on the film when the film is conveyed into the film receiving canister.

16. The goggle assembly of claim 13, wherein an upper portion of the edge protrudes further upstream in a film conveying direction than a lower portion of the edge.

17. The goggle assembly of claim 10, wherein the lens frame is disposed in a front portion of a goggle frame.

18. The goggle assembly of claim 10, wherein the lens frame is an adaptor attachable to a goggle frame.

19. A method comprising:

conveying a film from a film dispensing canister across a front surface of a lens to a film receiving canister; and collecting debris from the film at a continuous surface formed by an upper triangular surface of an upper wing portion, a sloping surface of a lower wing portion, and a lower triangular surface of a blade portion disposed between the upper and the lower wing portions of the film receiving canister before the film is conveyed into the film receiving canister;

wherein the upper triangular surface is provided at a bottom side of the upper wing portion and the lower triangular surface is provided at a top side of the lower wing portion, and wherein an upper portion of the upper triangular surface is curved to face toward the lower triangular surface and a lower portion of the lower triangular surface is curved to face toward the upper triangular surface, such that the continuous surface has a broad, U-shape.

20. The method of claim 19 further comprising directing the debris collected on the blade portion away from a field of view of the lens by a slanting edge of the blade portion.

* * * * *